(12) United States Patent
Nebosis

(10) Patent No.: US 8,559,016 B2
(45) Date of Patent: Oct. 15, 2013

(54) METHOD AND SYSTEM FOR OPTICAL COHERENCE TOMOGRAPHY

(75) Inventor: Rainer Nebosis, Munich (DE)

(73) Assignee: Agfa HealthCare NV, Mortsel (BE)

( * ) Notice: Subject to any disclaimer, the term of this patent is extended or adjusted under 35 U.S.C. 154(b) by 398 days.

(21) Appl. No.: 12/632,932

(22) Filed: Dec. 8, 2009

(65) Prior Publication Data

US 2010/0149543 A1 Jun. 17, 2010

(30) Foreign Application Priority Data

Dec. 16, 2008 (EP) ..................................... 08171873
Nov. 27, 2009 (EP) ..................................... 09177326

(51) Int. Cl.
*G01B 9/02* (2006.01)

(52) U.S. Cl.
USPC .............................................................. 356/497

(58) Field of Classification Search
USPC ................................................. 356/497, 479
See application file for complete search history.

(56) References Cited

U.S. PATENT DOCUMENTS

| | | | | |
|---|---|---|---|---|
| 5,465,147 A * | 11/1995 | Swanson | ........................ | 356/497 |
| 6,552,806 B1 * | 4/2003 | Swinford et al. | ............. | 356/512 |
| 7,088,454 B2 * | 8/2006 | Chang et al. | ................... | 356/497 |
| 8,199,327 B2 | 6/2012 | Nebosis et al. | | |
| 8,330,962 B2 | 12/2012 | Nebosis et al. | | |
| 8,339,610 B2 | 12/2012 | Nebosis et al. | | |
| 2003/0199769 A1 * | 10/2003 | Podoleanu et al. | ........... | 600/476 |
| 2004/0239946 A1 * | 12/2004 | Kane et al. | ..................... | 356/497 |
| 2004/0263859 A1 | 12/2004 | Chang et al. | | |
| 2005/0219544 A1 * | 10/2005 | Chan et al. | ..................... | 356/497 |
| 2010/0027020 A1 | 2/2010 | Nebosis | | |
| 2010/0027024 A1 | 2/2010 | Nebosis et al. | | |
| 2010/0027029 A1 | 2/2010 | Nebosis et al. | | |
| 2010/0033726 A1 | 2/2010 | Nebosis et al. | | |

(Continued)

FOREIGN PATENT DOCUMENTS

| | | |
|---|---|---|
| EP | 1962049 A1 | 8/2008 |
| EP | 1962050 A1 | 8/2008 |

(Continued)

OTHER PUBLICATIONS

Grieve, K., et al., "Ocular Tissue Imaging Using Ultrahigh-Resolution, Full-Field Optical Coherence Tomography,"Investigative Ophthalmology & Visual Science, vol. 45, No. 11, Nov. 2004, pp. 4126-4131.
Schmit J., et al., "Extended averaging technique for derivation of error-compensating algorithms in phase-shifting interferometry," Applied Optics, vol. 34, No. 19, Jul. 1, 1995, pp. 3610-3619.
Watanabe, Y. et al., "Full-field optical coherence tomography by achromatic phase sifting with a rotating polarizer," Applied Optics, vol. 44, No. 8, Mar. 10, 2005, pp. 1387-1392.
Watanabe, Y., et al., "In vivo non-mechanical scanning grating -generated optical coherence tomography using an InGaAs digital camera," Optics Communications 261, 2006, pp. 376-380.
Watanabe, Y., et al., "Three-dimensional wide-field optical coherence tomography using an ultrahigh-speed CMOS camera," Optics Communications 281, 2008, pp. 1889-1895.

(Continued)

*Primary Examiner* — Tarifur Chowdhury
*Assistant Examiner* — Jonathan Hansen
(74) *Attorney, Agent, or Firm* — Houston & Associates, LLP

(57) ABSTRACT

In a method and a system for optical coherence tomography, light, with which a specimen (1) is irradiated, is emitted by an interferometer (10), which comprises a beam splitter (13) and a reflector (12). Light reflected by the specimen (1) is collected by a detector (11), and the reflector (12) is brought into a number of positions at different optical distances away from the beam splitter (13). To record images of a specimen (1) easily and quickly, with high quality, the light reflected by the specimen (1) is collected a number of times by the detector (11) and converted into corresponding detector images, while the reflector (12) in the respective position is in the rest position. An averaged detector image is obtained for each position. A tomogram is generated from the averaged detector images obtained for the different positions of the reflector (12).

13 Claims, 1 Drawing Sheet

(56) References Cited

U.S. PATENT DOCUMENTS

| | | |
|---|---|---|
| 2010/0067022 A1 | 3/2010 | Nebosis et al. |
| 2010/0091295 A1 | 4/2010 | Nebosis et al. |
| 2010/0097616 A1 | 4/2010 | Nebosis et al. |
| 2010/0166293 A1* | 7/2010 | Sugita et al. ............... 382/154 |
| 2010/0280315 A1* | 11/2010 | Pan ............................ 600/109 |

FOREIGN PATENT DOCUMENTS

| | | |
|---|---|---|
| EP | 1962051 A1 | 8/2008 |
| EP | 1962052 A1 | 8/2008 |
| EP | 1962079 A1 | 8/2008 |
| EP | 1962080 A1 | 8/2008 |
| EP | 1962081 A1 | 8/2008 |
| EP | 1962082 A1 | 8/2008 |

OTHER PUBLICATIONS

Watanabe, Y., et al., "Three-dimensional imaging by ultrahigh-speed axial-lateral parallel time domain optical coherence tomography," Optics Express, vol. 14, No. 12, Jun. 12, 2006, pp. 5201-5209.

European Search Report dated May 8, 2009, from counterpart European Application No. EP 08171873.6, filed on Nov. 27, 2009.

* cited by examiner

METHOD AND SYSTEM FOR OPTICAL COHERENCE TOMOGRAPHY

RELATED APPLICATIONS

This application claims priority to European Patent Application No. EP08171873.6, filed on Dec. 16, 2008 and European Patent Application No. EP09177326.7, filed on Nov. 27, 2009, both of which are incorporated herein by reference in their entirety.

BACKGROUND OF THE INVENTION

Optical coherence tomography (OCT) is a method for investigating light scattering specimens. Biological tissue is particularly suitable for investigation by means of OCT due to its light-scattering properties. Since OCT only requires relatively low light intensities and the wavelengths of the light used mainly come within the near infrared range (750 nm to 1350 nm), it does not—unlike X-ray diagnostics—subject the biological tissue to any radiation.

Therefore, OCT is particularly significant for medicine and is comparable to ultrasound diagnostics, instead of noise, however, broadband light with a very short coherence length being used. The life spans of the light reflected on different boundary layers in the specimen are recorded with the aid of an interferometer. By means of OCT one can typically achieve resolutions one to two orders of magnitude higher than with ultrasound, however the maximum measuring depth is considerably smaller. Due to optical scattering the cross-sectional images obtained only reach to a depth of a few millimeters into the tissue. The currently most important fields of application for OCT are in opthalmology, dermatology and the diagnosis of cancer. However, there are also non-medical applications, such as e.g. materials testing.

It is known from Y. Watanabe et al., OPTICS COMMUNICATIONS 261 (2006) 376-380 and Y. Watanabe et al., APPLIED OPTICS Vol. 44, No. 8 (2005) 1387-1392 to record two-dimensional interference images from a specific depth of a specimen with different phase differences between the specimen and reference arm of the interferometer with a two-dimensional camera, and to calculate a two-dimensional image from this. An actuator adjusts the optical path length of a path of an optical interferometer. With a first position a measuring point is recorded. After this the path difference is changed, and a second measuring point recorded. A third measuring point is obtained in a similar way. The amplitude of the OCT signal is calculated from these three measuring values. With this method it cannot always be guaranteed that the image information from the inside of the specimen produced from the interference images obtained in this way have the quality required with specific diagnostic applications. Moreover, with this method very fast movement of the actuator is required in order to be able to avoid blurs caused by possible movement of the specimen. Moreover, very long down times result during which no images can be recorded.

An OCT method is known from US 2004/0263859 A1 wherein a tomogram of a specific layer within a body is established from a non-interference image ($I_d$) of a background and two interference images ($I_0$, $I_\Phi$) recorded with different phase positions. In order to reduce noise, the two interference images ($I_0$, $I_\Phi$) recorded with different phase positions are respectively obtained by averaging a number of interference images recorded at different times. With this method a high image quality of the tomogram obtained can not be guaranteed in all applications.

SUMMARY OF THE INVENTION

It is the object of the invention to specify a method and a corresponding system for optical coherence tomography wherein images of a specimen can be recorded easily and quickly with the highest possible quality.

With the method according to the invention a reflector of the interferometer is brought into a number of, preferably at least three, different positions different optical distances away from a beam splitter of the interferometer, and the light reflected at a specific depth of the specimen is collected a number of times by a detector and converted into corresponding detector images which are interference images, while the reflector is located in the respective position. This means that that for a specific finite depth within the specimen with a number of, preferably at least three, different reflector positions, a number of detector images, i.e. interference images, are obtained. The detector images obtained with the respective position of the reflector are then averaged so that for each of the positions of the reflector an averaged detector image, i.e. an averaged interference image, is obtained. From the averaged detector images obtained for the preferably at least three different positions a tomogram is finally generated.

The corresponding system according to the invention comprises an interferometer for emitting light with which a specimen is irradiated, having a beam splitter and at least one reflector, as well as a detector for collecting light which is reflected by the specimen. A control unit controls the system in such a way that the reflector is brought into a number of, preferably at least three, different positions different optical distances away from the beam splitter, the light reflected at a specific depth of the specimen is collected a number of times by the detector and converted into corresponding detector images, i.e. interference images, while the reflector is located in the respective position, the detector images obtained for the respective position of the reflector are averaged, respectively one averaged detector image, i.e. averaged interference image, being obtained, and a tomogram being established from the averaged detector images obtained for the different positions.

Unlike the method known from the prior art wherein a tomogram is derived from a non-interference image of the background and two averaged interference images from a specific layer of the specimen, with the method and system according to the invention tomograms are derived from preferably at least three averaged interference images recorded at a specific finite depth within the specimen.

The invention is based upon the idea of recording, with each of the—preferably three—different positions of the reference mirror, a number of N detector images from a specific finite depth within the specimen in individual measurements, and then averaging the latter to form respectively one averaged detector image. Since the individual detector images are obtained by collecting coherent light, one can therefore also talk of coherent averaging of the detector images. Only after the coherent averaging of the N detector images to form respectively one averaged detector image for each position of the reference mirror is a tomogram generated from the averaged detector images. This step is also called demodulation of the averaged detector images.

According to the invention, for this purpose an actuator is fitted in an optical interferometer for changing the path length difference step by step, N individual measurements being taken for each position of the actuator while the actuator remains unmoved. Only after this is the actuator further moved by a specific step size which is preferably ⅙ of the average wavelength of the light injected into the interferometer. N individual measurements are then in turn recorded. The same procedure is followed with the third position and, if applicable, any further positions. The respective N measurements of the different positions are averaged to form a respective one averaged detector image for each position, and only then demodulated.

In order to implement the method according to the invention a very fast camera is advantageous because the path length difference must not change substantially over the whole measuring process. Preferably, stability in the range of just a few nanometers (nm) is permissible here. Therefore, the whole measuring process should be shorter than one second. Moreover, it is advantageous to use a laterally incoherent light source, such as e.g. a halogen lamp, in order to avoid noise due to so-called speckle and intermodal cross talk in the case of fibre optic illumination.

Theoretical analyses have shown that with the coherent averaging according to the invention the signal-to-noise ratio is five times as great as with a method with incoherent averaging, i.e. with averaging of the detector images only after demodulation of the latter. With measurements, surprisingly even a one to 19 times higher signal-to-noise ratio was found than with incoherent averaging.

In comparison to methods according to the prior art, the actuator can be N times slower. Moreover, the down time, during which no detector images can be recorded, is only 1/N.

In conclusion it can be established that by means of the method and system according to the invention images of a specimen can be recorded easily and quickly with high image quality.

Preferably, light with an average wavelength is injected into the interferometer, and the reflector is brought into the number of different positions by displacing the reflector by one step size respectively, the step size being smaller than the average wavelength. In particular, the step size is one sixth of the average wavelength. In this way a particularly high image quality is guaranteed. Due to the very small step sizes, in the following this displacement of the reflector will also be called a microscopic displacement.

In a further preferred embodiment provision is made such that the reflector is brought into three different positions, and the detector images obtained for each of the three positions of the reflector are averaged so that for each of the three positions an averaged detector image is obtained, and from the averaged detector images obtained for the three positions a tomogram is established. In this way a high image quality is achieved, without at the same time perceptibly slowing down the image recording.

Preferably, an averaged intensity $I_0$, $I_{120}$ or $I_{240}$ is respectively assigned here to each pixel of the three averaged detector images from which corresponding pixels of the tomogram are established by demodulation. In particular, the pixels B of the tomogram are established here from the averaged intensities $I_0$, $I_{120}$ and $I_{240}$ as follows:

$$B = \frac{1}{9} \cdot [(2I_{120} - I_0 - I_{240})^2 + 3(I_0 - I_{240})^2]$$

By means of the demodulation of the averaged detector images undertaken in this way, a tomogram is obtained reliably and quickly.

It is, moreover, advantageous to collect the light reflected by the specimen with the detector at least 50 times, and to convert it into at least 50 corresponding detector images, while the reflector is located in the respective position. By means of this measure too, high image quality is achieved, and at the same time here the speed of the image recording is not substantially slowed down.

Preferably, the light reflected by the specimen is collected by the detector in the form of two-dimensional detector images at an image rate of at least 1000 detector images per second. For this purpose, a high-speed camera with a two-dimensional detector surface is used as a detector. In this way adverse effects upon the image quality due to shaking of the specimen during the measuring process are greatly reduced. With most applications it is in this way guaranteed that the path length difference due to shaking of the specimen during a measurement only changes within a range of a few nanometers (nm).

Moreover, it is preferred that the average wavelength of the light injected into the interferometer comes within approximately 1100 nm and approximately 1500 nm. In addition to a larger penetration depth into the specimen, in this way a high image quality is also guaranteed.

The light to be injected into the interferometer is advantageously generated by a thermal light source, in particular by a halogen light source, and filtered through a spectral Gaussian filter. In this way noise due to so-called speckle and intermodal cross talk in the case of fibre optic illumination is avoided, and correspondingly the image quality is further increased.

In a further advantageous embodiment of the invention provision is made such that the light reflected by the specimen and detected by the detector originates from a specific depth of the specimen, and the depth is set by changing the distance between the reflector and/or a reflector objective located between the beam splitter and reflector, and the beam splitter, preferably by additionally changing the position of a specimen objective located between the beam splitter and the specimen, the change of the distance or the position being substantially greater than the average wavelength of the light injected into the interferometer. In contrast to the microscopic change, described above, of the reflector position by fractions of the average wavelength, the change made to the distance between the reflector or reflector objective and the beam splitter when setting the depth can be called a macroscopic change.

In this way a so-called depth scan or z scan is produced by the optical distance between the reflector and the beam splitter respectively being changed step by step by macroscopic optical paths of typically 0.1 mm to a number of millimeters, and then respectively the light reflected by the specimen being collected by the two-dimensional detector in the manner according to the invention. Due to the macroscopic change of the optical distance between the reflector and the beam splitter, the depth ranges in which the so-called coherence condition for the occurrence of interference is fulfilled migrate through the specimen, and so the light reflected by individual planes at these depths of the specimen can interfere with the light reflected by a reference mirror. The respectively occurring manifestations of interference are recorded by the two-dimensional detector as detector images, and are averaged. The coherence condition indicates, among other things, that the light waves reflected respectively by the specimen and the reference mirror must have a constant phase relationship to one another in order to be able to interfere with one another. Since the light injected into the interferometer generally has a very short coherence length of typically 10 μm, the condition of a constant phase relationship is only fulfilled at specific depths or depth ranges of the specimen which are therefore also called a coherence gate. Therefore, every position of the reflector corresponds to a specific depth or a range around this specific depth within the specimen for which the coherence condition is fulfilled, and so interference can occur between the light reflected by the reference mirror and the light reflected at this depth of the specimen.

In comparison with the systems and methods known from the prior art, in this way images can be recorded more easily and more quickly from different depths of the specimen. In particular, one can dispense with a moveable stage for changing the distance of the specimen relative to the interferometer.

With this embodiment, provision is made, moreover, such that light emitted by the interferometer through the specimen objective is focused in a focus lying in or on the specimen, additionally to the macroscopic change of the optical distance between the reflector and the beam splitter the imaging properties of the specimen objective also being controlled such that the focus comes within the range of the respective depth of the specimen. By means of this so-called focus tracking it is achieved that the light collected with different positions of the reflector from different depths of the specimen are always imaged with the greatest possible sharpness onto the detector elements of the detector disposed in one area.

In one particularly advantageous embodiment of the invention the microscopic displacement of the reflector by one step size respectively, which is smaller than the average wavelength, is implemented by a first drive, and the macroscopic change of the distance between the reflector and/or the reflector objective and the beam splitter, which is substantially greater than the average wavelength of the light injected into the interferometer, by a second drive which is different from the first drive.

Preferably, the reflector and the reflector objective are coupled to the first drive and the second drive such that the second drive can displace the reflector and the reflector objective together, and the first drive can only displace the reflector alone. A piezoelectric actuator, which is attached to a holder and is coupled to the reflector, is used, for example, as a first drive. A spindle driven by a motor and which is coupled by a spindle nut to the holder to which, in addition to the reflector, the reflector objective is also attached, is used, for example, as the second drive.

By means of the separate drives for the microscopic reflector movement on the one hand, and the macroscopic movement of the reflector and of the reflector objective on the other hand, firstly the problem is resolved whereby drives, which can generate macroscopic strokes can generally not be sufficiently stabilised such that with the coherent averaging according to the invention the reflector could be brought sufficiently precisely into a sufficiently still position. Moreover, the problem is eliminated whereby with fast microscopic movements, as are implemented when approaching the respective positions, not only the reflector, but also the reflector objective must also be moved, by means of which, due to the overall relatively large overall mass post oscillation of the reflector brought into a specific position would be the result, and one would have to wait until the light reflected by the specimen is collected until the post oscillation has abated, and the reflector is still. However, this would delay the recording of the detector images in the respective position, and so slow down the process.

Preferably, the second drive is designed as a self-locking drive. This is to be understood as a drive with which slipping or rotating of the component, i.e. the reflector or reflector objective, brought by the drive into a specific position or location, is prevented by means of resistance caused by friction. Self-locking is achieved, for example, by a precision spindle driven by a motor and which is coupled to the reflector or reflector objective by means of a pre-tensioned spindle nut.

If a specific position of the reflector or reflector objective is achieved, this is substantially held by frictional forces between the spindle and the spindle nut, and so active regulation for holding the position is not required, and the motor can be switched off. In the case of a non-self-locking drive, however, an active regulation circuit for holding the position would be required, and this would however generally lead to the reflector or the reflector objective oscillating to and fro around its desired position. These—even if very small oscillation deflections—would make the coherent averaging according to the invention impossible if the latter were greater than approximately 50 nm. A self-locking second drive can in contrast be switched off after reaching the desired position so that no oscillation deflections occur, and a precise microscopic displacement of the reflector by means of the first drive is guaranteed.

Due to the use according to the invention of two separate drives, on the one hand a reliable and solid macroscopic displacement of the reflector, including the reflector objective, is thus achieved in order to guarantee sharp imaging of the reflector onto the detector in all of the set depths of the specimen, and on the other hand precise, vibration-free and fast microscopic positioning of the reflector is made possible when recording detector images in microscopically different positions at a specific depth of the specimen.

In an alternative version of the invention provision is made such that the reflector, together with the reflector objective located between the beam splitter and the reflector, is displaced by one step size respectively, and is thus brought into the number of different positions different optical distances away from the beam splitter, the step size being smaller than the average wavelength. The macroscopic change of the distance between the reflector and the reflector objective and the beam splitter when setting a specific depth on the one hand, and the microscopic movement of the reflector and of the reflector objective in order to choose the different positions on the other hand, can with this version only be accomplished by a common drive, e.g. an appropriate actuator.

In a further embodiment of the invention, after determining a tomogram, the reflector remains in its last adopted end position. Only after setting another depth from which the light reflected by the specimen and detected by the detector originates is the reflector then moved from its end position, step by step via one or more intermediate positions, back into its initial position, the light reflected by the specimen being collected a number of times by the detector, and being converted into corresponding detector images while the reflector is located in the respective position. In this way consecutive recording of a number of tomograms from different depths of the specimen is clearly accelerated, and this contributes to keeping the time used to generate a three-dimensional tomogram of the specimen from a number of two-dimensional tomograms within limits.

Moreover, it is preferred that when averaging the detector images only the detector images obtained with the respective position of the reflector are used which have been recorded at times when the reflector in the respective position was in a rest position. Here, with the respective averaging, only those detector images are used which were recorded at times outside of, i.e. before or after, the change of position of the reflector. In particular, these times are located a sufficient interval after a change of the position of the reflector in order to avoid any adverse effect upon the image quality due to vibrations of the reflector which can occur directly after the change in position. This measure also contributes to increasing the image quality without substantially slowing down the speed of recording the image.

Within the context of the invention, irradiation of the specimen with the light emitted by the interferometer is to be understood as meaning that the light emitted by the interferometer, which comprises the moveable reflector, strikes the specimen directly or only strikes the specimen after passing through a further interferometer which is disposed between the interferometer and the specimen.

Within the context of the invention, collection of the light reflected by the specimen, in particular at different depths of the specimen, by the detector is to be understood as meaning that the detector collects the light from manifestations of interference which occur upon superimposition of the light reflected by the specimen, in particular at different depths of the specimen, with the light reflected on a reference mirror. Here the superimposition of the light can take place either in the interferometer, which comprises the moveable reflector, or in a further interferometer.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
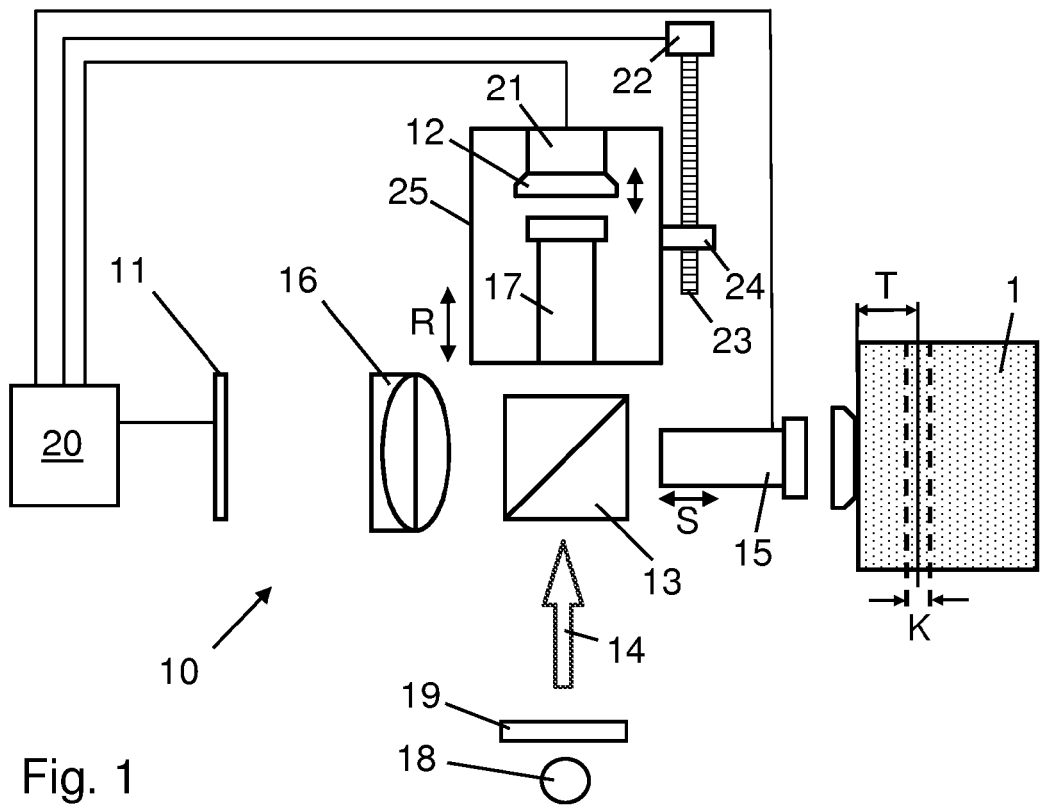
FIG. 1 is schematic diagram showing an exemplary embodiment of the OCT system according to the invention.

FIG. 1 shows a first exemplary embodiment of the OCT system according to the invention having an interferometer 10, which comprises a moveable reference mirror 12 as a reflector, a beam splitter 13, a specimen objective 15, a detector objective 16, a reference objective 17 and a detector 11, and a control unit 20 for controlling the system.

Into the interferometer 10 light 14 is injected which is obtained by spectrally filtering the light emitted by a light source 18, in particular a halogen lamp. The spectral filtering is implemented by an optical filter 19 the spectral transmission of which follows a Gaussian-shaped course, and which is therefore also called a spectral Gaussian filter. The average wavelength λ of the light 14 injected into the interferometer 10 comes between approximately 1100 nm and 1500 nm.

The injected light 14 is split by the beam splitter 13 into a first partial beam in the direction of the specimen objective 15 and a second partial beam in the direction of the reference objective 17. The first partial beam crosses the specimen objective 15, strikes a specimen 1, is reflected by the latter, then passes through the specimen objective 15 again and is superimposed in the beam splitter 13 with the second partial beam reflected on the reference mirror 12 to form a third partial beam which is imaged by the detector objective 16 onto the two-dimensional detector 11 and recorded by the latter as a detector image.

The detector 11 is preferably a semiconductor detector in CMOS technology and has a plurality of detector elements (pixels) arranged in an area, the number of which is typically 640×512 pixels. Due to the simultaneous "parallel" recording of a plurality of reflections at different locations in a plane E at a specific depth T of the specimen 1 made possible by this, this type of OCT can also be called parallel OCT. Preferably, the detector 11 is a high-speed camera with which the individual detector images can be recorded at an image rate of at least 1000 detector images per second.

The plane E located at a depth T beneath the specimen surface, from which detector images are recorded, is reached by a change of the distance between the reference mirror 12 and/or the reference objective 17 and the beam splitter 13 by a path in direction R which is considerably greater than the average wavelength λ of the light 14 injected into the interferometer 10. By simultaneously changing the position of the specimen objective 15 in the direction S relative to the beam splitter 13 it is achieved that the focus of the first partial beams passing through the specimen objective 15 comes respectively within the coherence gate K so that the interference signals obtained from the plane E from the depth T and the sharpness of the detector images recorded by the detector 11, i.e. the interference patterns, are maximal for all depths T in the specimen 1. The change of the distance between the reference mirror 12 and/or the reference objective 17 and the specimen objective 15 and the beam splitter 13 is preferably achieved by means of spindle drives, which in turn are driven, for example, by stepper motors.

Moreover, the reference mirror 12 is coupled to an actuator 21 by means of which the reference mirror 12 is displaced by one step respectively, and is thus brought into a number of different positions. In contrast to the specification described above of a specific depth T within the specimen 1, the step size here is, however, only a fraction, preferably a sixth, of the average wavelength λ of the light 14 injected into the interferometer. The actuator 21 is preferably in the form of a piezoelectric actuator with which these positions can be set easily and extremely precisely.

The actuator 21 coupled to the reference mirror 12 is attached to a holder 25 into which, in addition to the reference mirror 12, the reference objective 17 is also integrated. The holder 25 is coupled by means of a spindle nut 24 to a precision threaded spindle 23 which is driven by a stepper motor 22. By means of this embodiment it is achieved that in order to set a specific depth T within the specimen 1 the reference mirror 12, together with the reference objective 17, is moved by macroscopic distances, while the setting of the preferably three different positions of the reference mirror 12 when collecting the light reflected at the depth T is achieved by a microscopic displacement only of the reference mirror 12 by means of the actuator 21.

In an alternative version of the system the drive (not shown) for changing the distance between the reference mirror 12 and/or the reference objective 17 and the beam splitter 13 is designed such that, in addition to macroscopic position changes with step sizes with are considerably greater than the average wavelength λ of the light 14 injected into the interferometer 10, it can implement a microscopic movement of the reference mirror 12 and of the reference objective 17 with a step size which is only a fraction of the average wavelength λ of the light 14 injected into the interferometer. This microscopic movement must be implemented very precisely with an error of just a few nanometers. With this version one can dispense with the additional actuator 21 for setting the different positions of the reference mirror 12.

In the example shown in FIG. 1 the stepper motor 22, the drive (not shown) of the specimen objective 15, the actuator 21 and the detector 11 are controlled by the control unit 20 in the manner such that in each position of the reference mirror 12 a plurality of detector images are recorded for a specific depth T within the specimen 1. Preferably, for each position at least 50 detector images are recorded which are then averaged so that an averaged detector image is obtained for each position. The averaged detector images obtained with different positions of the reference mirror 12 for a specific depth T within the specimen 1 are then subjected to a demodulation by means of which a tomogram, i.e. a two-dimensional image, of plane E, located at depth T, of the specimen 1 is finally obtained.

Figure 2:
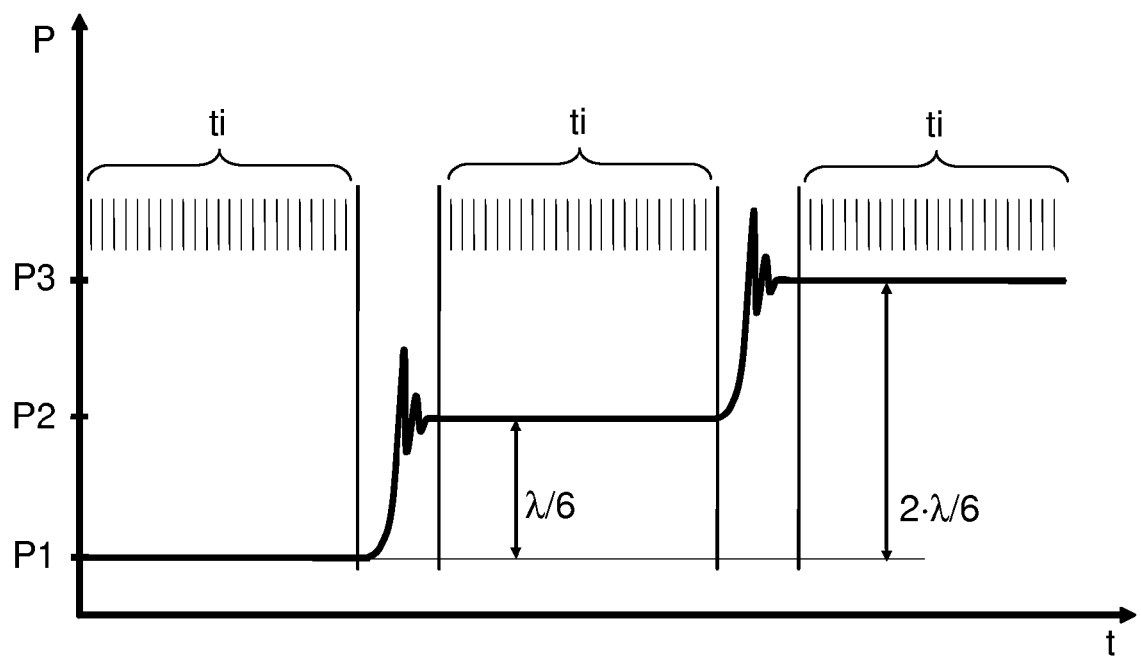
FIG. 2 is a plot of mirror position as a function of time illustrating the method according to the invention.

This is described in greater detail in connection with the diagram shown in FIG. 2. The diagram shows a course of the over the time t. Starting from a first position P1, after a specific first period of time the reference mirror 12 is brought into a second position P2 with the aid of the piezoelectric actuator 21 by displacing by a step size $\lambda/6$. After a further second period of time the reference mirror 12 is brought by a further step size $\lambda/6$ into a third position P3. The distance between the third position P3 and the first position P1 is then $2\cdot\lambda/6$. Before reaching the second and the third position P2 or P3 the reference mirror 12 passes through a respective transient effect which can be recognised by the oscillations in the course of the positions P.

Over the period of time during which the reference mirror 12 is located in the first, second and third positions P1, P2 and P3 a plurality of consecutive detector images is respectively recorded by the detector 11. The detector images obtained with each of positions P1, P2 and P3 are averaged, for each of positions P1, P2 and P3 an averaged detector image being obtained. With the respective averaging only those detector images obtained with a position P1, P2 or P3 which were recorded at times outside of the displacement of the reference mirror in 12, in particular outside of the transient effects of the reference mirror 12, are used. These times ti, at which the reference mirror 12 was in the rest position, are identified in the diagram shown by short, vertical lines.

In this way, for the first position P1 a first averaged detector image $I_0$, for the second position P2 a second averaged detector image $I_{120}$, and for the third position P3 a third detector image $I_{240}$ are obtained. In this case, the respective indices 0, 120 and 240 stand for a phase difference of 0°, 120° or 240° which is generated by a displacement of the reference mirror 12 by 0, $\lambda/6$ or $2\lambda/6$.

From the averaged detector images $I_0$, $I_{120}$ and $I_{240}$ a tomogram B of the plane E located at depth T of the specimen 1 is finally calculated as follows:

$$B = \frac{1}{9} \cdot [(2I_{120} - I_0 - I_{240})^2 + 3(I_0 - I_{240})^2]$$

In this way further tomograms B of planes E at other depths T within the specimen 1, which can optionally be added to a three-dimensional tomogram, can be obtained.

Preferably, the reference mirror 12 is not moved back into its initial position, in this case the first position P1, after establishing a tomogram B, but it remains in its last adopted position, in this case the third position P3, and is moved from the latter, step by step, back into its initial position. After setting another depth T of the plane E, in the example described above, therefore, detector images are initially recorded, while the reference mirror 12 is located in the third position P3, and then averaged. After this detector images are recorded in the second position P2 and finally in the first position P1, and after this are respectively averaged. In this way the recording of a larger number of tomograms is substantially accelerated.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for optical coherence tomography, comprising:
    injecting light with an average wavelength into an interferometer;
    irradiating a specimen with light emitted by the interferometer, the interferometer comprising a beam splitter and a reflector;
    collecting light reflected by the specimen with a detector;
    bringing the reflector into at least three different rest positions having different optical distances away from the beam splitter by displacing the reflector by one step size, respectively, the step size being smaller than the average wavelength;
    while the reflector is located in each of the at least three different rest positions, collecting the light reflected by the specimen at a specific depth of the specimen a number of times by the detector and converting the light into a number of corresponding interference images, wherein the interference images are obtained by collecting coherent light;
    coherent averaging the interference images obtained by collecting coherent light for each of the at least three different rest positions of the reflector by using only those interference images obtained with each of the at least three rest positions of the reflector which were recorded at times at which the reflector in the respective position was located in a rest position, wherein an averaged interference image is obtained for each of the at least three different rest positions of the reflector, to obtain at least three averaged interference images; and
    after coherent averaging of said number of interference images is obtained for each of the at least three rest positions of the reflector, demodulating the at least three averaged interference images obtained for the at least three different rest positions of the reflector to obtain a two-dimensional image of a plane E located at depth T within the specimen.

2. The method according to claim 1, further comprising:
    assigning an averaged intensity respectively to each pixel of the three averaged interference images; and
    establishing pixels of the tomogram from the averaged intensities.

3. The method according to claim 1, further comprising, while the reflector is located in the respective position, collecting the light reflected by the specimen at least 50 times by the detector and converting the light at least 50 corresponding interference images.

4. The method according to claim 1, further comprising generating the light injected into the interferometer with a thermal light source.

5. The method according to claim 1, wherein
    while the reflector is located in each of the at least three rest positions, the light reflected by the specimen and detected by the detector originates from a specific depth of the specimen, and the depth is set by a change of the distance between the reflector and the beam splitter, or between a reflector objective and the beam splitter, said change being substantially greater than the average wavelength of the light injected into the interferometer.

6. The method according to claim 5, wherein the displacement of the reflector by one step size respectively, which is smaller than the average wavelength, is implemented by a first drive, and the change of the distance between the reflector and the reflector objective or between the reflector and the beam splitter, which is substantially greater than the average wavelength of the light injected into the interferometer, being implemented by a second drive which is different from the first drive.

7. The method according to claim 6, further comprising the second drive displacing the reflector and the reflector objective together, the first drive only displacing the reflector alone.

8. The method according to claim 1, further comprising, after establishing a tomogram, keeping the reflector in its last adopted end position, and after setting a different depth, from which the light reflected by the specimen and detected by the detector originates, moving the reflector from the end position step by step via one or more intermediate positions back into its initial position, the light reflected by the specimen being collected a number of times by the detector and being converted into corresponding interference images, while the reflector is located in the respective position.

9. A system for optical coherence tomography comprising:
an interferometer for receiving light with an average wavelength and for emitting light with which a specimen is irradiated, the interferometer comprising a beam splitter and at least one reflector;
a detector for collecting light which is reflected by the specimen; and
a control unit for bringing the reflector into at least three different rest positions having different optical distances away from the beam splitter, wherein the reflector is displaceable by one step size, respectively, the step size being smaller than the average wavelength, wherein, while the reflector is located in each of the at least three different rest positions, the light reflected by the specimen at a specific depth of the specimen is collected a number of times by the detector and converted into a number of corresponding interference images, wherein the interference images are obtained by collecting coherent light, the interference images obtained for each of the at least three rest positions of the reflector being obtained by using only those interference images obtained with each of the at least three rest positions of the reflector and wherein the interference images are coherent averaged by the control unit, wherein an averaged interference image is obtained for each of the at least three different positions of the reflector, and after coherent averaging of said number of interference images obtained for each of the at least three rest positions of the reflector, for demodulating the at least three averaged interference images obtained for the at least three different rest positions to obtain a two-dimensional image of a plane E located at depth T within the specimen.

10. The system according to claim 9, further comprising:
a first drive for displacing the reflector by one step size respectively into the at least three different positions, the step size being smaller than an average wavelength of light injected into the interferometer, and
a second drive to change the distance between the reflector and a reflector objective located between the beam splitter and the reflector, or between the reflector and the beam splitter, the change of the distance being substantially greater than the average wavelength of the light injected into the interferometer, and the second drive being different from the first drive.

11. The system according to claim 10, wherein the second drive is in the form of a self-locking drive.

12. The system according to claim 10, wherein the reflector and the reflector objective are coupled to the first drive and to the second drive with the second drive displacing the reflector and the reflector objective together, and the first drive only displacing the reflector alone.

13. A method according to claim 1, further comprising:
repeating the method for further specific depths T in the specimen, wherein each of the further specific depths T is set by a change of the distance between the reflector and the beam splitter or between a reflector objective, said reflector objective being located between the beam splitter and the reflector, and the beam splitter, the change of the distance being greater than the average wavelength of the light injected into the interferometer, and
adding two-dimensional images of planes E located at respective depths T within the specimen to a three-dimensional tomogram.

* * * * *